US006852132B1

(12) United States Patent
Houser et al.

(10) Patent No.: US 6,852,132 B1
(45) Date of Patent: Feb. 8, 2005

(54) ARTIFICIAL LIMBS INCORPORATING SUPERELASTIC SUPPORTS

(75) Inventors: Russell A. Houser, Livermore, CA (US); William D. Hare, Bethesda, MD (US)

(73) Assignee: Russell A Houser, Livermore, CA (US)

( * ) Notice: Subject to any disclaimer, the term of this patent is extended or adjusted under 35 U.S.C. 154(b) by 0 days.

(21) Appl. No.: 10/187,878

(22) Filed: Jul. 3, 2002

Related U.S. Application Data (63) Continuation of application No. 09/965,542, filed on Sep. 27, 2001, and a continuation-in-part of application No. 09/898,577, filed on Jul. 3, 2001, now Pat. No. 6,718,656
(60) Provisional application No. 60/302,978, filed on Jul. 3, 2001, provisional application No. 60/295,839, filed on Jun. 6, 2001, provisional application No. 60/272,110, filed on Feb. 28, 2001, provisional application No. 60/236,923, filed on Sep. 28, 2000, and provisional application No. 60/216,045, filed on Jul. 5, 2000.

(51) Int. Cl.[7] ................................................. A61F 2/66
(52) U.S. Cl. ............................................ 623/52; 623/55
(58) Field of Search ......................... 623/27–46, 47–56; 901/27–29, 30–31, 8

(56) References Cited

U.S. PATENT DOCUMENTS

| | | | | |
|---|---|---|---|---|
| 5,858,020 A | * | 1/1999 | Johnson et al. | .......... 623/23.15 |
| 6,379,393 B1 | * | 4/2002 | Mavroidis et al. | ............ 623/25 |

* cited by examiner

*Primary Examiner*—Alvin Stewart (57) ABSTRACT

A method of using an artificial limb includes mounting an artificial limb to a body part, applying a force to the artificial limb to deflect the artificial limb from a first position in a first direction, and removing the force, whereby the artificial limb moves to the first position. The artificial limb includes a mounting end configured to be mounted to a body part and one or more superelastic members. The superelastic members may be made of Nitinol.

16 Claims, 10 Drawing Sheets

ARTIFICIAL LIMBS INCORPORATING SUPERELASTIC SUPPORTS

CROSS-REFERENCE TO RELATED APPLICATIONS

This application claims priority from U.S. Provisional Patent Application No. 60/302,978, filed Jul. 3, 2001, titled "Artificial Limbs Incorporating Superelastic Supports." This application also claims priority from and is a continuation of U.S. patent application Ser. No. 09/898,577, filed Jul. 3, 2001, now U.S. Pat. No. 6,718,656 titled "Shoes and Braces with Superelastic Supports," which claims priority from U.S. Provisional Application Ser. No. 60/216,045, filed Jul. 5, 2000, titled "Shoes and Braces with Superelastic Supports."

This application also claims priority from and is a continuation of U.S. patent application Ser. No. 09/965,542 filed Sep. 27, 2001, titled "Joint Braces and Traction Devices Incorporating Superelastic Support," which claims priority from U.S. Provisional Application Ser. No. 60/236,923,filed Sep. 28, 2000 titled "Anatomic Braces with Superelastic Support;" U.S. Provisional Application Ser. No. 60/272,110, filed Feb. 28, 20001, titled "Additional Anatomic Braces and Scaffolds with Superelastic Supports;" and U.S. Provisional Application No. 60/295,839, filed Jun. 6, 2001, titled "Traction Devices Incorporating Superelastic Supports"; each of which is incorporated in their entirety by reference.

TECHNICAL FIELD

This invention relates to devices for replacing specific anatomic limb regions of amputees, and restoring the performance of nonfunctional or less viable anatomic appendages. More particularly, the invention relates to supports that are incorporated in artificial limbs and braces to restore functionality of the appendages.

BACKGROUND

Current techniques for providing artificial limbs or braces involve using stainless steel, carbon fiber laminate and composites, or semi-rigid polymers to replace the anatomic appendage. These conventional artificial limbs are extremely stiff and do not provide a broad range of dynamic response to the user during movement of the artificial limb. As such, conventional artificial limbs limit the normal degree of bending, shock absorption, rotation, and force exerted upon movement of the artificial appendage.

Conventional brace configurations incorporate stainless steel, or other solid metal or alloy bar attached to the brace and incorporating a hinge to enable movement of the bar about the joint. These current braces are typically bulky, heavy, and severely limit any motion of the anatomy—thus they do not restore near-normal performance of the appendage. In addition they greatly inhibit the rotation, bending, or other motion that inherently produces an applied force and elicits a desired response (e.g., standing, walking, running, hitting, throwing, or other activity).

A need thus exists for artificial limbs and braces that incorporate superelastic supports capable of being deflected a predetermined amount in response to an external force and exert an opposing force in response to the deflection. As such these artificial limbs and braces help to restore motion of the anatomy despite loss of limb functionality. The artificial limbs and braces also reinforce the anatomic structures, and prevent excess twisting, bending, or other motion capable of resulting in injury. In addition there is a need for artificial limbs and braces that provide a predetermined resistance to motion so as to gradually restore motion to the nonfunctional limb, and stabilize or strengthen anatomic structures during rehabilitation or training processes.

SUMMARY OF THE INVENTION

In one general aspect, an artificial limb includes a mounting end configured to be mounted to a body part and one or more superelastic members.

Embodiments of the artificial limb may include one or more of the following features. For example, at least one of the superelastic members may be connected to the mounting end.

The artificial limb may further include a second superelastic member extending from a first superelastic member. The first superelastic member has a first orientation, the second superelastic member has a second orientation, and the first orientation is generally perpendicular to the second orientation. The second superelastic member may include a curved section. The second superelastic member may include Nitinol. The second superelastic member may include a pair of generally parallel superelastic members.

The first superelastic member may include a curved section. One or more of the superelastic members may include Nitinol.

One or more of the superelastic members may include a pair of generally parallel superelastic members.

The artificial limb may further include a third superelastic member extending in a generally perpendicular direction from the first superelastic member such that a force of flexing the first superelastic member in the direction of the second superelastic member is counteracted by the third superelastic member contacting the second superelastic member.

In another general aspect, using an artificial limb includes mounting an artificial limb to a body part, applying a force to the artificial limb to deflect the artificial limb from a first position in a first direction, and removing the force such that the artificial limb moves to the first position. The artificial limb includes a mounting end configured to be mounted to a body part and one or more superelastic members.

Embodiments of the method of using an artificial limb may include one or more of the following features. For example, mounting an artificial limb to a body part may include placing a tightening link around the body part. Mounting an artificial limb to a body part may include inserting the body part into a concave housing. Applying a force to the artificial limb may include bending the one or more superelastic members and/or pressing the artificial limb against a surface. The superelastic materials may include Nitinol.

In another general aspect, fabricating an artificial limb includes cutting one or more superelastic materials to a desired length, forming the superelastic material into a desired resting configuration of an artificial limb using a fixture that has or imparts the desired resting configuration, heating the superelastic material to between 300 degrees Celsius and 750 degrees Celsius, cooling the superelastic material, and removing the superelastic material from the fixture.

Embodiments of the method of fabricating the artificial limb may include one or more of the following features. For example, forming the superelastic material into a desired configuration may include forming the superelastic material into the shape of one or more of a foot, a leg, and an arm.

The superelastic material may include Nitinol.

The embodiments of the present invention provide artificial limbs and braces containing superelastic supports that elastically return towards their baseline, or annealed configuration when deflected by an external force. As such these superelastic supports may be utilized in artificial limbs and braces to restore motion of the nonfunctional limb by producing an opposing force upon deflection to aid standing, walking, running, jumping, throwing, rotating, hitting, shooting, swinging, or other motion associated with physical activity.

The embodiments of the present invention also reinforce the anatomic structures, apply localized continuous compressive force against specific anatomic structures, and/or stabilize anatomic structures. As such, the artificial limbs and braces aid in healing by reinforcing specific regions and relieving stress exerted upon other regions of the body during motion of artificial limbs, or nonfunctional or less viable appendages.

The artificial limbs and braces also prevent excessive or unwanted twisting, bending, or other movement capable of causing injury or excessive stress to the anatomical joint or structures. As such, the muscles, tendons, bone interconnections, and other anatomy that enable movement at the joints are reinforced so they are less susceptible to being exposed to excess tension, stress, strain, or torque. The superelastic artificial limbs and braces of the invention also preserve the flexibility at the joint, facilitate the response to motion about the joint, and/or intensify the force exerted during movement of anatomic structures about the joint. As such, the artificial limbs and braces provide motion assistance to aid the wearer in performing an activity. In particular, the superelastic supports of the artificial limbs and braces enhance standing, bending, throwing, kicking, jumping, running, walking, hitting, shooting, or other strenuous activity by providing a directional force in response to an opposing deflection.

The artificial limbs and braces of the invention are intended to restore functionality of an amputated or nonfictional anatomic appendage. The artificial limbs and braces also reinforce the knees, ankles, elbows, wrists, shoulders (especially the rotator cuffs), neck, hips, or other anatomic joint associated with the amputated or nonfunctional anatomic appendage. The artificial limbs and braces also enable applying a specific force to tailor movement of the appendages and gradually restore operation. Artificial limbs and braces having adjustable force characteristics and/or degrees of motion may be used during the healing and training process to vary the amount of motion and strengthen tissue required to accommodate increased functionality.

The above described features, and many further features, and advantages of the present invention will be elaborated in the following detailed description and accompanying drawings.

DETAILED DESCRIPTION

The following is a detailed description of the presently best-known modes of carrying out the inventions. This detailed description is not to be taken in a limiting sense, but is made merely for the purpose of illustrating the general principles of the inventions.

This specification discloses a number of embodiments, mainly in the context of appendage replacement, reinforcement, and performance enhancement for artificial limbs, and braces. The appendages that the embodiments may be modified to address include the foot, the leg below the knee, the leg extending above the knee, the hand, the arm below the elbow, the arm extending above the elbow, and the arm including the shoulder. Two or more artificial limbs and braces of the invention may be combined with a variety of mechanisms that are able to coordinate the operation of the artificial limbs and braces to satisfy the performance requirements for multiple replaced appendages or nonfunctional limbs.

Nevertheless, it should be appreciated that the structures are applicable for use in other indications involving devices that are used to replace anatomic structures, exert continuous force against anatomic structures once positioned, restrict motion to a desired track, and/or exert a desired force in response to an externally induced deflection. The artificial limbs are configured for the human anatomy; however, it should be noted that the artificial limbs can be tailored to other species, such as horses, dogs, and cats, by changing the geometry and sizes of the structures.

The artificial limbs provide supports fabricated from superelastic shape memory alloys. These superelastic supports elastically deform upon exposure to an external force and return towards their preformed shape upon reduction or removal of the external force. The superelastic support members may exhibit stress-induced martensite characteristics in that they transform from the pre-shaped austenite form to the more soft and ductile martensite form upon application of stress and transform back toward the more strong and hard austenite form once the stress is released or reduced. These characteristics depend on the composition of the superelastic shape memory alloys, which affects the temperature transition profile. Superelastic shape memory alloys also enable straining the material numerous times without plastically deforming the material. Superelastic shape memory alloys are light-weight and exhibit excellent tensile strengths, which allows them to be advantageously used as artificial limbs, traction devices, joint braces, anatomic scaffolds, guards, or shields, or other devices without dramatically increasing the weight of the device, or making the device thick or bulky. The utility of superelastic materials in supports for artificial limbs, traction devices, and joint braces is highlighted by the inherent properties of such materials; namely, they are able to withstand continuous and frequent deflections without plastically deforming or observing fatigue failures.

These supports may also be elastically deflected into small radii of curvatures and return towards their preformed configuration once the external force causing the deflection is removed or reduced. Many other known metal, alloy, and thermoplastic materials plastically deform or break when deflected into a similar small radius of curvature or exposed to comparable strains. As such these other metal, alloy, and thermoplastic materials do not return towards their original configuration when exposed to the amount of deflection such supports are expected to endure. Therefore superelastic supports may inherently incorporate flex regions, which conventional artificial limbs and braces are unable to accommodate, thereby eliminating the need for two or more components being connected through a hinge structure that requires pivot points between the two or more components. As such, superelastic artificial limbs and braces better preserve normal motion of the replaced or nonfunctional appendage.

Superelastic supports also are able to apply force by taking advantage of the spring characteristics of such materials thereby providing dynamic response of the replaced or nonfunctional appendage during motion. Moreover, the complexity and cost of artificial limbs and braces that incorporate superelastic supports is significantly reduced when compared to conventional artificial limbs and braces. Moreover, superelastic supports permit deflections into smaller radii of curvature than other metals, alloys, and polymers resulting in larger strains. Superelastic supports also are capable of exerting substantial force when deflected, ensuring that the superelastic supports return towards their preformed shape after being elastically deformed.

Superelastic supports are preferably fabricated from shape memory alloys (e.g., nickel titanium) that demonstrate stress-induced martensite at ambient temperature. Of course, other shape memory alloys may be used and the superelastic material may alternatively exhibit austenite properties at ambient temperature. The composition of the shape memory alloy is preferably chosen to produce the finish and start martensite transformation temperatures (Mf and Ms) and the start and finish austenite transformation temperatures (As and Af) depending on the desired material response.

When fabricating shape memory alloys that exhibit stress induced martensite the material composition is chosen such that: (1) the maximum temperature at which the material exhibits stress-induced martensite properties (Md) is greater than Af; and (2) the range of temperatures between Af and Md covers the range of ambient temperatures to which the support members are exposed. When fabricating shape memory alloys that exhibit austenite properties and do not transform to martensite in response to stress, the material composition is chosen such that both Af and Md are less than the range of temperatures to which the supports are exposed. Of course, Af and Md may be chosen to be set at any temperature provided the shape memory alloy exhibits superelastic properties throughout the temperature range to which they are exposed. Nickel titanium having an atomic ratio of 51.2% Ni and 48.8% Ti exhibits a Af of approximately −20° C.; nickel titanium having an atomic ratio of 50% Ni to 50% Ti exhibits a Af of approximately 100° C. [Melzer A, Pelton A. Superelastic Shape-Memory Technology of Nitinol in Medicine. *Min Invas Ther & Allied Technol.* 2000: 9(2) 59–60].

Such superelastic materials are able to withstand strain as high as 10% without plastically deforming. As such, these superelastic materials are capable of elastically exerting a force upon deflection. Materials other than superelastic shape memory alloys may be used as supports provided they can be elastically deformed within the temperature, stress, and strain parameters required to maximize the elastic restoring force because this type of deformation enables the artificial limb or brace to exert a directional force in response to an induced deflection. Such materials include other shape memory alloys, bulk metallic glasses, amorphous Beryllium, suitable ceramic compositions, spring stainless steel 17-7, Elgiloy™, superelastic polymers, etc.

The embodiments of the invention provide artificial limbs and braces for any anatomic appendage. In particular, the artificial limbs and braces of the invention contain superelastic supports that exert forces in response to an external deflection to mimic the normal operation of the replaced or reinforced appendage. In addition, the artificial limbs and braces are capable of preventing excess twisting, abnormal rotation, unwanted bending or other deleterious motion capable of causing injury to the muscles, tendons, bones, or other anatomic structures around the appendages.

By exerting a directional force in response to an opposing deflection, these superelastic supports mimic motion of replaced or nonfunctional appendages, such as the foot, leg, hand, and arm. As such, superelastic limbs and braces help restore the ability to perform daily activities such as standing, walking, running, lifting, hitting, throwing, shooting, swinging, kicking, jumping, or other physical motion by utilizing the elastic recoil of the supports to institute representative forces exerted by the appendages.

The embodiments of the invention provide artificial limbs and braces for the foot, leg, hand, and arm that incorporate superelastic supports to restore operation of replaced or nonfunctional appendages. The superelastic artificial limbs and braces address the needs of pre-op, post-op, and rehabilitative patient by providing the flexibility to change the stiffness and the amount of elastic recoil required during the specific phase of treatment or recovery.

For all artificial limb and brace embodiments containing superelastic supports described below, the supports may be embedded in a flexible covering (not shown in all drawings). The covering may only cover individual supports or may encompass all or a subset of superelastic supports between covering layers. The covering may be fabricated from expanded and regular polytetrafluoroethylene (PTFE), neoprene, fabric mesh, LYCRA™, SPANDEX™, leather, chamois, silicone, polyurethane, rubber, PEBAX™, Dacron™, nylon, polyester, other cushioning materials typically used in braces that demonstrate excellent elasticity, or a combination of these materials. Since the superelastic supports provide the replacement and/or reinforcing structure, the covering may be fabricated to be extremely thin. This further ensures the artificial limb or brace is capable of maintaining or enhancing the motion of the joint and does not hinder movement of the anatomy about the joint.

The covering may be attached to the superelastic supports by dipping the supports, laminating layers around the supports, adhesively bonding layers together and/or to the supports, ultrasonic welding, thermal bonding, radio frequency welding, laser welding the layers, sewing, injection molding, sintering, other manufacturing process capable of encompassing the superelastic supports between layers of covering, or a combination of these bonding processes. The covering layers may be attached to each other and/or the supports when embedding the supports within layers of covering material. The covering layers may be fabricated with perforations to wick away sweat, provide pathways for air to pass, or for other purposes.

The superelastic supports (e.g., reference numeral 200 of FIGS. 1*a* and 1*b*) of the artificial limbs and braces are fabricated in the desired pattern of links (e.g., tightening links, spring links, and/or links having other purposes and characteristics) to tailor the desired spring characteristics, radial stiffness, and axial stiffness to optimize the artificial limb or brace to the desired motion or dynamic response. The ability to change parameters of the various links may be accomplished by the inherent properties of the thermally formed superelastic supports, or other components may be used to change the geometry, attachment points, lengths, other variable, or a combination of variables that affect the links' spring characteristics. The superelastic supports may contain any number of tightening links, spring links, and/or links having other purposes and characteristics.

The superelastic supports may be fabricated from at least one rod, wire, band, bar, tube, sheet, strip, ribbon, other raw material having the desired pattern, cross-sectional profile, and dimensions, or a combination of cross-sections. The superelastic supports are cut into the desired pattern and are thermally formed into the desired 3-dimensional geometry. Alternatively, the superelastic supports may be fabricated as a plane for their preformed orientation, and secured as a three-dimensional geometry around the joint by tying opposite ends with knots, applying Velcro™ or other attachment means between opposite ends, or using other removable securing process. The rod, wire, band, bar, sheet, tube, strip, ribbon, or other raw material may be fabricated by extruding, molding, press-forging, rotary forging, bar rolling, sheet rolling, cold drawing, cold rolling, using multiple cold-working and annealing steps, casting, or otherwise forming into the desired shape. Then the supports must be cut into the desired length and/or pattern. Conventional abrasive sawing, water jet cutting, laser cutting, EDM machining, photochemical etching, or other etching techniques may be employed to cut the supports from the raw material.

Ends or any sections of the rod, wire, band, sheet, tubing, strip, ribbon, or other raw material may be attached together, or along the length of the sections, by laser welding, adhesively bonding, soldering, spot welding, combination, or other attachment means. This attachment encloses the superelastic supports to provide additional reinforcement, eliminate edges, or other purpose. Multiple rods, wires, bands, sheets, tubing, ribbons, other raw materials, or a combination of these may be bonded to produce a composite superelastic support and form the skeleton of the artificial limb or brace.

For several of the artificial limb embodiments below, the superelastic supports are fabricated from at least one rod, band or bar of nickel titanium material cut to the desired length and thermally formed into the desired three-dimensional configuration. Alternatively, wire, sheet, tube, ribbon, a combination of these geometries, or other geometry of superelastic supports may be used. When thermally forming superelastic supports, the superelastic material(s), which are previously cut into the desired pattern and/or length, are stressed into the desired resting configuration using a forming fixture having the desired resting shape of the artificial limb or brace, and the material is heated to between 300 and 750 degrees Celsius for a period of time, typically between 15 seconds and 10 minutes. Once the volume of superelastic material reaches the desired temperature, the superelastic material is quenched by it inserting into chilled water or other fluid, or otherwise allowed to return to ambient temperature. As such the superelastic supports are fabricated into their resting configuration. When extremely small radii of curvature are desired, multiple thermal forming steps may be utilized to sequentially bend the rod, wire, band, sheet, strip, tubing, ribbon or other raw material into smaller radii of curvature to prevent overstressing/straining of the material.

When fabricating the superelastic supports from tubing, the raw material may have an oval, circular, rectangular, square, trapezoidal, or other cross-sectional geometry capable of being cut into the desired pattern. After cutting the desired pattern of tightening links and support links, the supports are formed into the desired shape, heated, for example, between 300° C. and 750° C., and allowed to cool in the preformed geometry to set the shape of the support members.

When fabricating the supports from flat sheets of raw material, the raw material may be configured with at least one width, W, and at least one wall thickness, T, throughout the raw material. As such, the raw sheet material may have a consistent wall thickness, a tapered thickness, or sections of varying thickness. The raw material is then cut into the desired pattern of tightening links and/or spring links, and thermally shaped into the desired 3-dimensional geometry. Opposite ends or intersections of thermally formed support members may be secured by using rivets, shrink tubing, applying adhesives, welding, soldering, mechanically engaging, utilizing another bonding means, or a combination of these bonding methods. Opposite ends of the thermally formed supports may alternatively be free-floating to permit increased flexibility.

Once the supports are fabricated and formed into the desired 3-dimensional geometry, the supports may be electropolished, tumbled, sand blasted, chemically etched, ground, or otherwise treated to remove any edges and/or produce a smooth surface.

Holes, slots, grooves, notches, other cut-away areas, or regions of ground material may be incorporated in the support design to tailor the stiffness profile of the support. Such holes, slots, grooves, notches, or other cut-away areas are also beneficial to increasing the bond strength or reliability when attaching the covering(s) to the superelastic supports. Cutting and treating processes described above may be used to fabricate the slots, holes, grooves, notches, cut-away regions, and/or ground regions in the desired pattern to taper the stiffness along the support, focus the stiffness of the supports at the tightening links, reinforce the spring links of the support, or otherwise customize the stiffness profile of the brace.

Figure 1A:
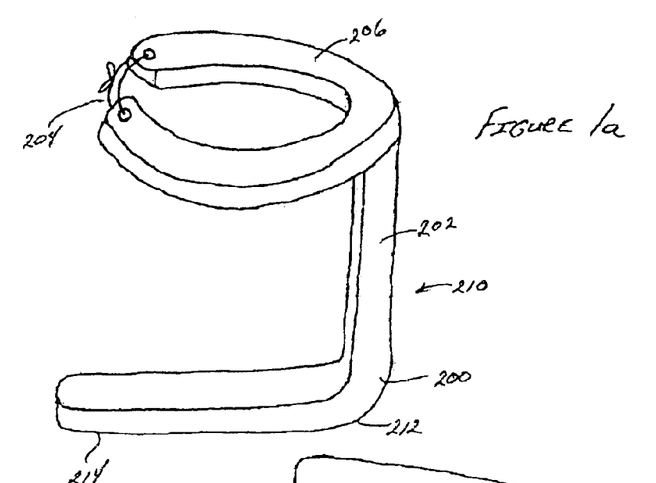
FIGS. 1a and 1b show perspective views of two artificial foot embodiments fabricated from superelastic supports.
Figure 1B:
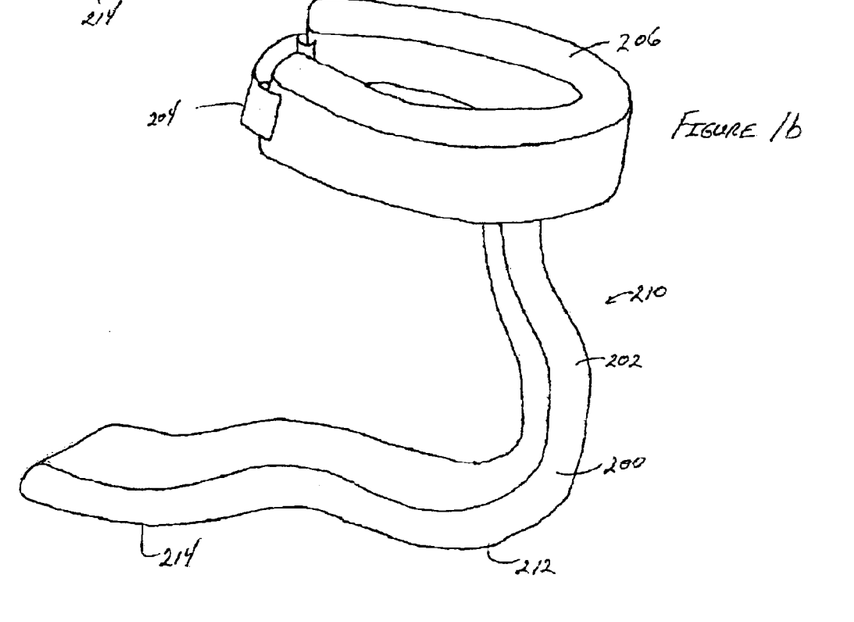

FIGS. 1*a* and *b* show perspective views of two artificial foot embodiments 210 fabricated from at least one superelastic support 200. These artificial foot embodiments incorporate at least one superelastic support (e.g., a single rod, band, or bar having a diameter or thickness between approximately 0.040" and 0.500" or larger) that is thermally formed into the desired three-dimensional geometry. This geometry is designed to define at least one spring link that mimics the natural motion of a foot relative to a leg and produce an integrated hinge and force feedback mechanism capable of applying this dynamic response to an artificial limb. The length, distribution and the characteristics of the superelastic support(s) determine the response of the artificial limb and the amount of force and location of the applied force(s) the artificial limb is capable of exerting. The superelastic supports have at least one width and at least one height for bars and bands (at least one diameter for rods), and at least one length configured to produce the desired stiffness and force profile. The width and/or height may vary throughout the superelastic supports to vary the stiffness profile and resulting response to movement. The length of the superelastic supports may be tailored to address varying attachment locations relative to the leg, yet still preserve the desired motion of the artificial foot relative to the leg.

The artificial foot embodiments in FIGS. 1a and b incorporate a spring link 202 mimicking the motion of an ankle. The spring link 202 defines the integrated hinge, which permits flexion of the artificial foot and determines the response of the artificial foot to such flexion. During manufacture, the cross-section of each superelastic support link may be a circular rod, a rectangular band, a rectangular bar, or other geometry that provides the desired stiffness to impart the reinforcing and spring forces. The superelastic support links 202 of FIGS. 1a and 1b are a rectangular bar thermally formed into the desired pattern. The artificial foot embodiments in FIGS. 1a and 1b incorporate at least one tightening link 206 attached to the spring link 202. The tightening link 206 may be attached with mechanisms specified previously or may be a continuation of the spring link, especially if the superelastic supports are fabricated from a sheet or tubing of raw material. It should be noted that the orientation of the superelastic support links relative to the leg depends on the purpose for the artificial limb and helps dictate the restriction of abnormal motion and the spring characteristic of the artificial limb. The embodiment in FIG. 1a has a spring link 202 extending from a tightening link 206 in an "L" shape. The spring link 202 in FIG. 1b incorporates a distinct ankle region, heel region 212, and toe region 214 to better represent the natural motion of the foot relative to the leg. The spring links 202 permit the desired amount of movement of the artificial limb and exert a desired amount of elastic recoil in response to an induced deflection. It should be noted that any number of spring links might be chosen depending on the manufacturing process, the desired spring constant, and the desired stiffness profile.

The tightening links 206 in these embodiments are configured to enlarge in response to an external force to enable positioning the artificial limb over the leg and return towards their preformed shape once positioned. The external force causing the tightening links 206 to enlarge may consist of spreading segments of the tightening links apart, or otherwise manipulating the tightening links to produce an expanded diameter. Once the tightening links 206 are allowed to return towards their resting configuration, the tightening links 206 provide a suitable compression around the leg regions to stabilize the position of the spring links and ensure suitable operation of the artificial limb. The tightening links 206 are further attached to the leg using locking bands 204 that may be secured with Velcro™ attachment mechanisms, ratchet locking mechanisms, buckling means, screw-type mechanism, or other attachment components. In FIGS. 1a and 1b, the locking bands 204 are used to secure each of the tightening links to the leg.

The superelastic supports of the artificial foot in FIGS. 1a and 1b may be thermally formed at any orientation between straight and bent at the maximum deflection an ankle allows. The spring links 202 are pre-shaped to orient the artificial foot at the desired resting orientation, depending on the desired activity. When the superelastic supports are pre-shaped in a generally straight position, the artificial foot is biased towards the resting, straight position. When the leg is deflected backwards during walking, running, kicking, or other motion, the energy causing the spring links 202 to deflect produces a spring force that produces an elastic recoil of the spring links once the deflection force is reduced or removed, consistent with a running, walking, or kicking motion. The stiffness of the spring links 202 determines the force required to deflect the spring links and the amount of elastic recoil. When the superelastic supports of the artificial foot are thermally formed such that the resting orientation is the bent position, reflecting the orientation of the foot at the any predetermined point during the walking, or running motion, a stored energy is produced when the spring links 202 are deflected towards the straight orientation. Once the deflection force causing the spring links 202 to straighten is reduced or removed, the elastic recoil of the spring links 202 causes the artificial foot to return towards the bent orientation, increasing the force exerted during walking or running.

Figure 2A:
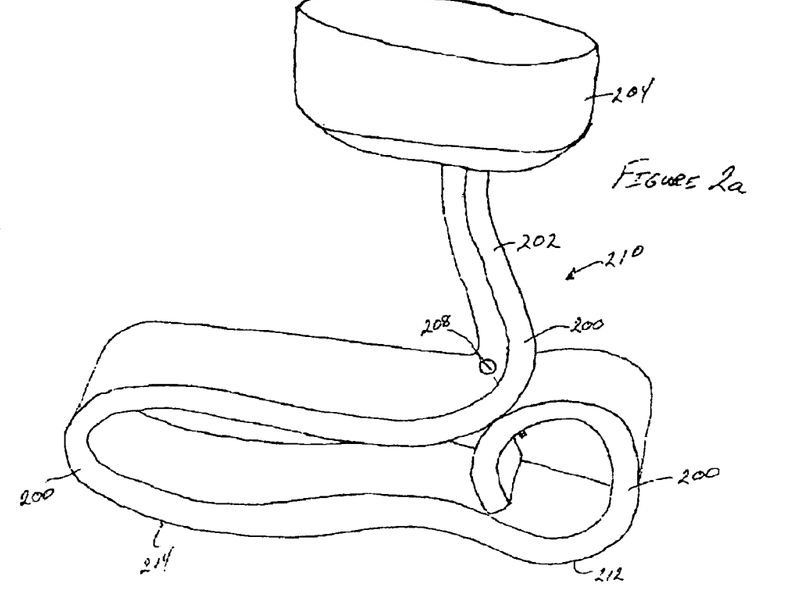
FIGS. 2a and 2b show perspective views of two additional artificial foot embodiments fabricated from superelastic supports.
Figure 2B:
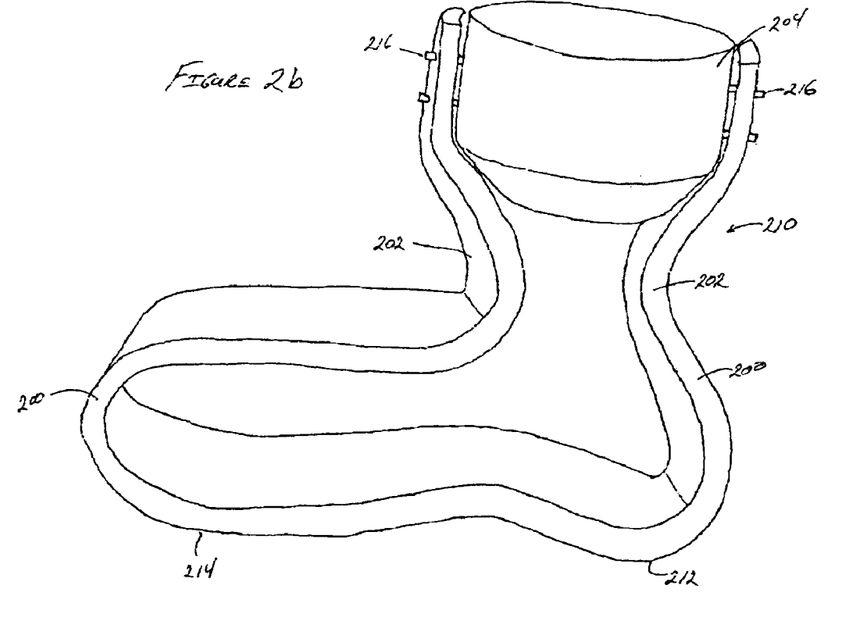

FIGS. 2a and 2b show alternative artificial foot embodiments in which the superelastic supports are fabricated as spring links 202 formed into substantially the same profiles as a foot. The spring links 202 are attached to distinct leg securing mechanisms 204. The embodiment in FIG. 2a has a single spring link 202 attached to the bottom of the leg securing mechanism 204 using the bonding processes previously described. The leg securing mechanism 204 may consist of a tightening link fabricated from a separate superelastic support or the same material, or a separate attachment housing designed to fit and secure the free end of the leg. The leg securing mechanism 204 may consist of a concave hollow housing designed with the appropriate compliance and geometry to fit and grip the leg. The interior of the housing may have a smooth or concave surface or surfaces to assist with the vacuum sealing. A valve port may be attached to the housing and provide a conduit to produce a vacuum in the housing by attaching the port to a suction source. The valve stem assembly would incorporate a release feature to enable breaking the vacuum seal to remove the leg end from the housing. The stem assembly can be placed, for example, on the base of the side of the housing. Although an external vacuum source can be applied to the valve stem to provide a vacuum, the vacuum also can be formed by merely placing body part in the housing while the valve is open. Then, when the body part is in the housing, the valve is closed such that the body part cannot be removed because it forms a vacuum within the housing. This provides improved attachment between the leg end and the leg securing mechanism. Alternatively, the discrete leg securing mechanism may consist of Pylons, mechanical mechanisms such as straps collars, laces, ties, a combination of securing means or other mechanism.

As previously stated, the spring link 202 may have any desired length to address various leg free end locations. The length may be adjustable so the wearer may tailor the location of the artificial foot spring link 202 relative to the leg. The embodiment in FIG. 2a incorporates a single spring link 202 attached to the leg securing mechanism 204. The spring link 202 extends to the base of the artificial foot, extends towards the toe 214 where it curves around to define the toe region of the foot 214, forms an arch for the artificial foot, and spirals around to produce the heel 212 of the artificial foot. The junction of the spring link from the ankle region to the base is secured to the heel spiral with an interconnect 208 which comprises rivets, screws, ultrasonic welding, laser welding, radio-frequency welding, or other bonding process.

The artificial foot embodiment shown in FIG. 2b incorporates a superelastic support 200 extending from the front of the leg securing mechanism 204 to the ankle region, curving around to define the toe 214 of the artificial foot, profiling the arch of the foot, curving to form the heel 212 of the artificial foot, and extending to the rear of the leg securing mechanism 204. The superelastic support 200 is secured to the front and rear of the leg securing mechanism 204 using an attachment means 216 consisting of rivets, screws, ultrasonic welding, laser welding, radio-frequency welding, or other bonding process. The looping superelastic support 200 of the embodiment shown in FIG. 2b provides independent deflection of the front spring link 202 and rear spring link 202. This provides better feedback to the wearer to improve balance and provide enhanced motion of the artificial foot.

Figure 3:
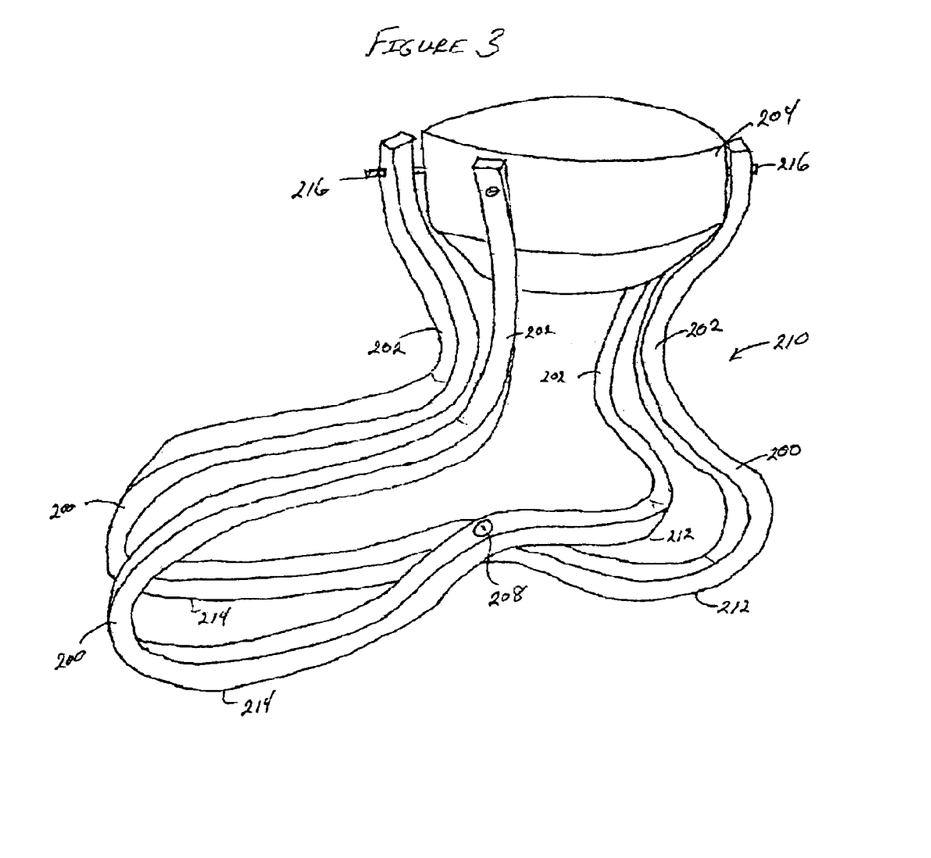
FIG. 3 shows a perspective view of an alternative artificial foot embodiment that incorporates multiple superelastic supports collaborating to improve the performance of the artificial foot.

FIG. 3a shows a perspective view of an alternative artificial foot embodiment 210 that incorporates two superelastic supports 200 intersecting along the arch of the foot. The ends of each superelastic support 200 are attached to the front and rear of the leg securing mechanism 204 using attachment means 216 as previously described. The intersection of the superelastic supports 200 are bonded with an interconnect 208 as previously described. Incorporating multiple superelastic supports improves the performance of the artificial foot by providing lateral support of the artificial foot and giving the wearer feedback that improves balance. Two superelastic supports 200 are shown looping from the front to the rear of the leg securing mechanism 204 in FIG. 3. It should be noted that more than two superelastic supports 200 may be used and the additional superelastic supports 200 may be formed so they intersect the original two superelastic supports 200 at different locations. Incorporating multiple superelastic supports may provide enhanced lateral support, improved stiffness profile between the toe and heel of the artificial foot, and/or heightened spring characteristics of the artificial foot.

Figure 4:
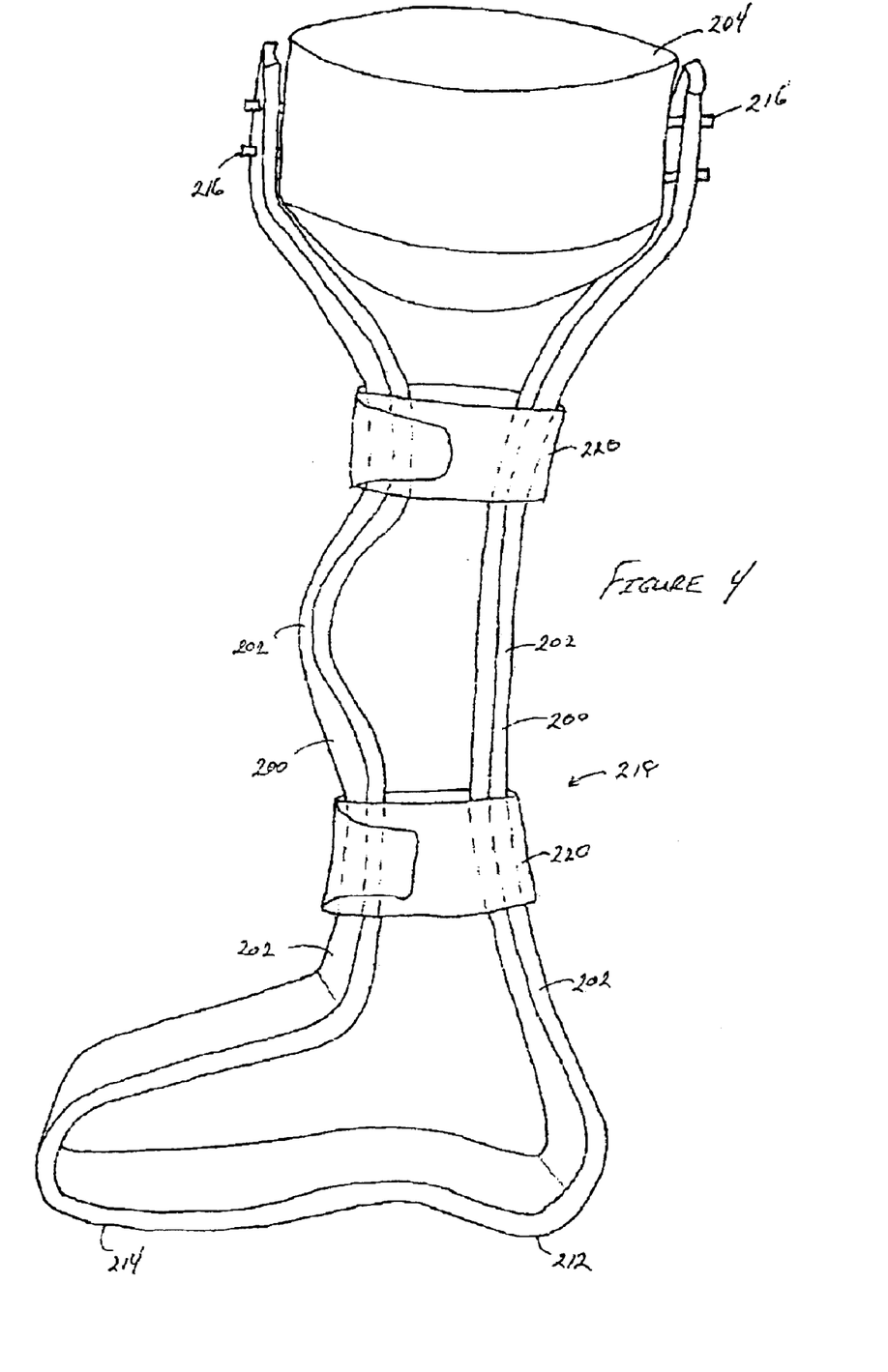
FIG. 4 shows a perspective view of an artificial leg embodiment fabricated from at least one superelastic support formed to provide dynamic response at the knee and ankle regions.

FIG. 4 shows a perspective view of an artificial leg extending above the knee consisting of a series of spring links 202 designed to restore movement of the leg at the foot, the ankle, and the knee. This artificial leg incorporates at least one superelastic support 200 extending from the front of the leg securing mechanism 204, around the knee and ankle regions of the artificial leg, looping around the toe and heel region of the foot and extending to the rear of the leg securing mechanism 204. The at least one superelastic support is securing to the leg securing mechanism 204 with attachment means 216 as previously described. Stiffening straps 220 lock the position of the front section and rear section of the superelastic support 200 together above the knee region and below the knee region to define the knee and enable adjusting the characteristics of the artificial leg 218. By tightening the stiffening straps 220 or moving the stiffening straps 220 towards the knee, the knee is stiffened and the elastic recoil of the knee spring link is increased. The lower stiffening strap tightness and location also affects the characteristics of the ankle region. The stiffening straps 220 provide the wearer the flexibility to change the characteristics of the artificial leg to optimize the response to a specific activity such as walking, running, standing, etc. The artificial leg embodiment in FIG. 4 consists of a single superelastic support 200 thermally formed into the pattern of spring link sections shown. Of course, multiple superelastic supports 200 may alternatively be used to form the artificial leg 218. Interconnecting mechanisms 208 (not shown) may be used to attach segments or free ends of the superelastic support(s) 200.

Figure 5A:
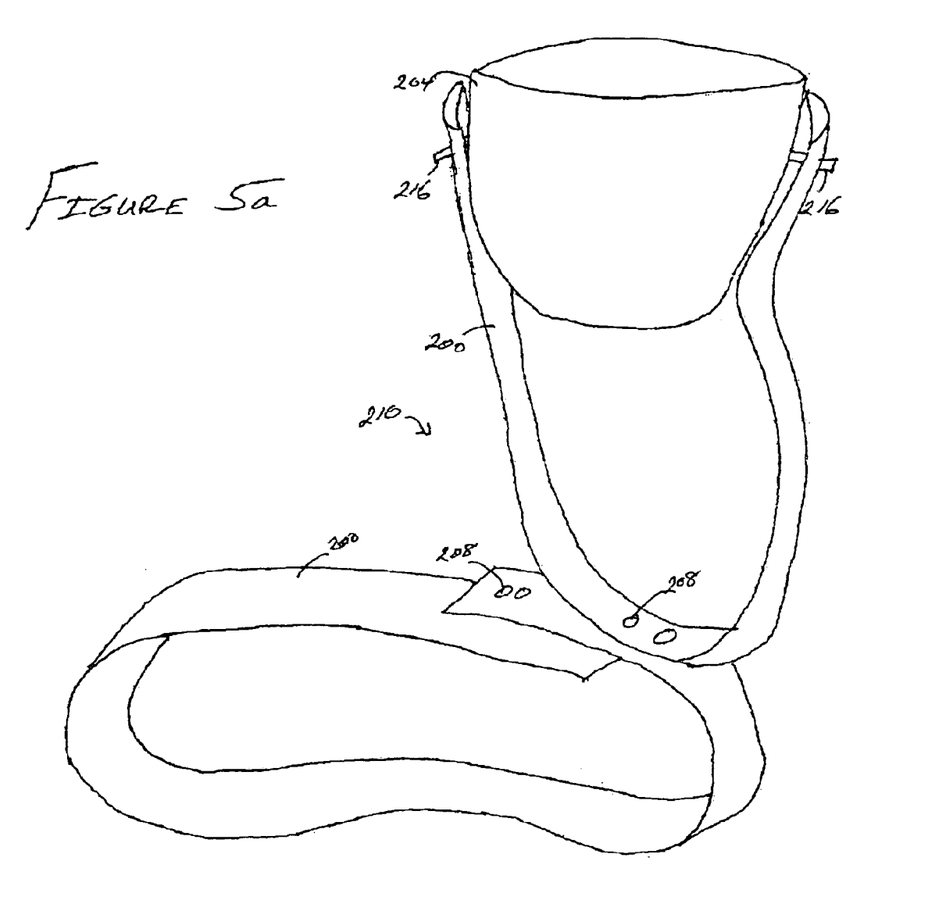
FIGS. 5a–c show perspective views of artificial leg embodiments fabricated from two superelastic supports formed to provide dynamic response at the ankle region.
Figure 5B:
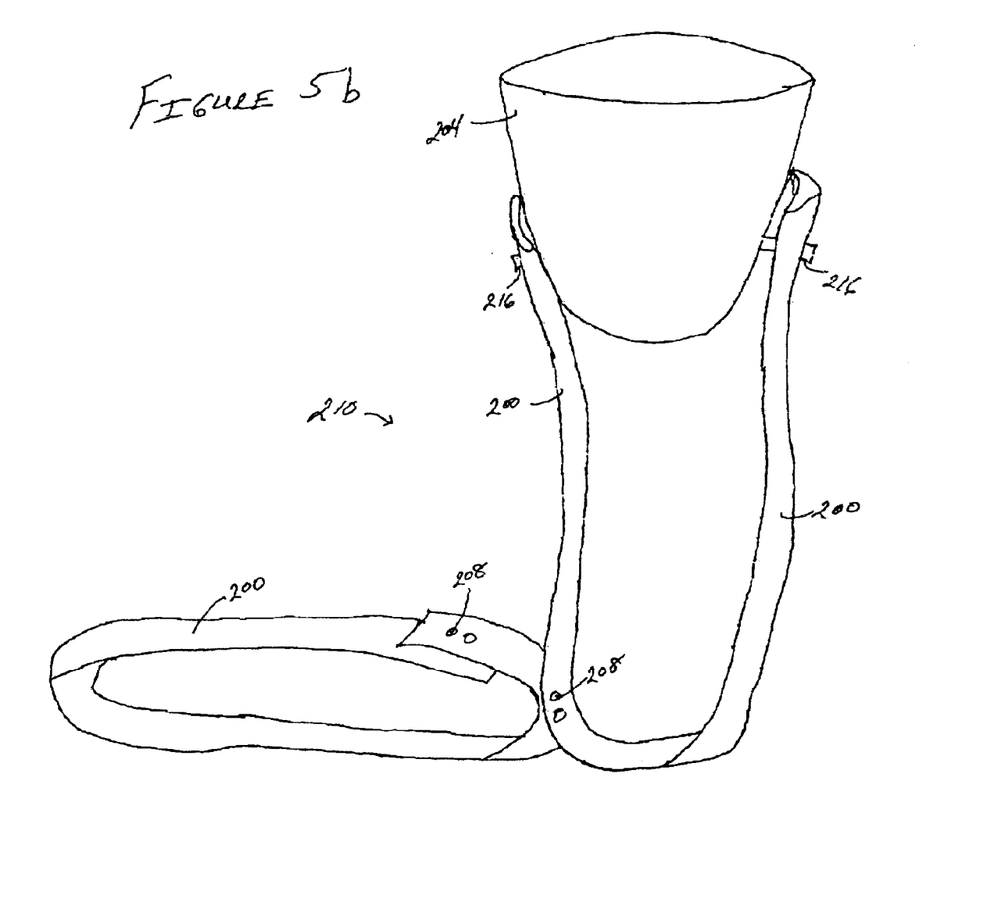
Figure 5C:
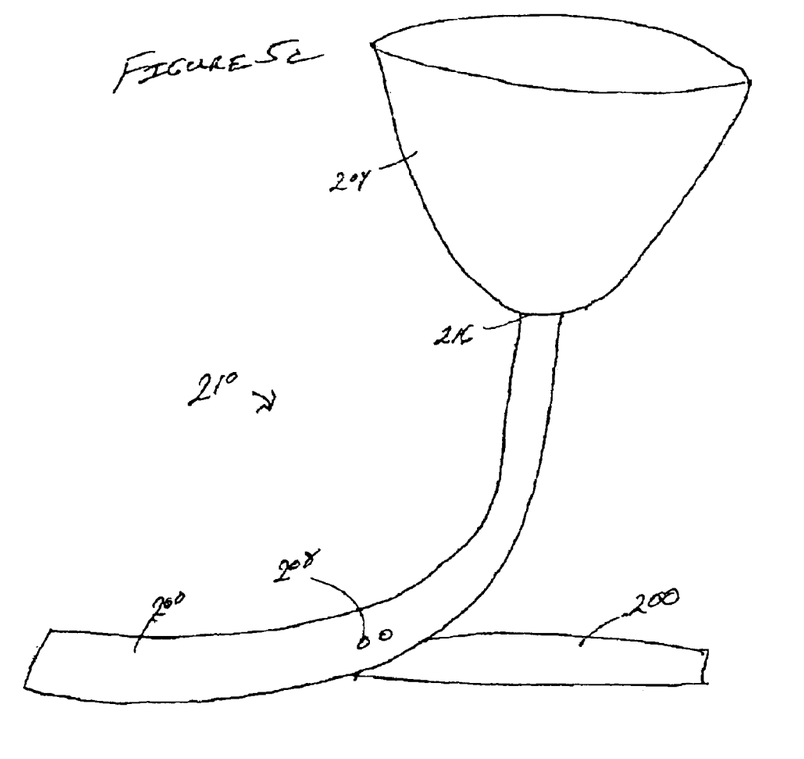

FIGS. 5a–c show perspective views of alternative artificial foot embodiments 210 that incorporate two superelastic supports 200, a first defining the foot, and the second defining the shin. The second superelastic support 200 is attached to the leg securing mechanism 204 using attachment means 216 as previously described. The first superelastic support is attached to the second superelastic support so as to define a flex point mimicking the natural motion of the ankle. The ends of each superelastic support are bonded together to enclose each superelastic support into a complete loop. Incorporating multiple superelastic supports to mimic natural flex point of anatomic joints improves the performance of the artificial foot by providing more realistic movement of the artificial foot and giving the wearer feedback that improves balance. It should be noted that more than two superelastic supports 200 may be used and the additional superelastic supports 200 may be formed so they intersect the original two superelastic supports 200 at different locations. Incorporating multiple superelastic supports may provide enhanced lateral support, an improved stiffness profile at the flex points of the artificial foot, and/or heightened spring characteristics of the artificial foot.

Figure 6:
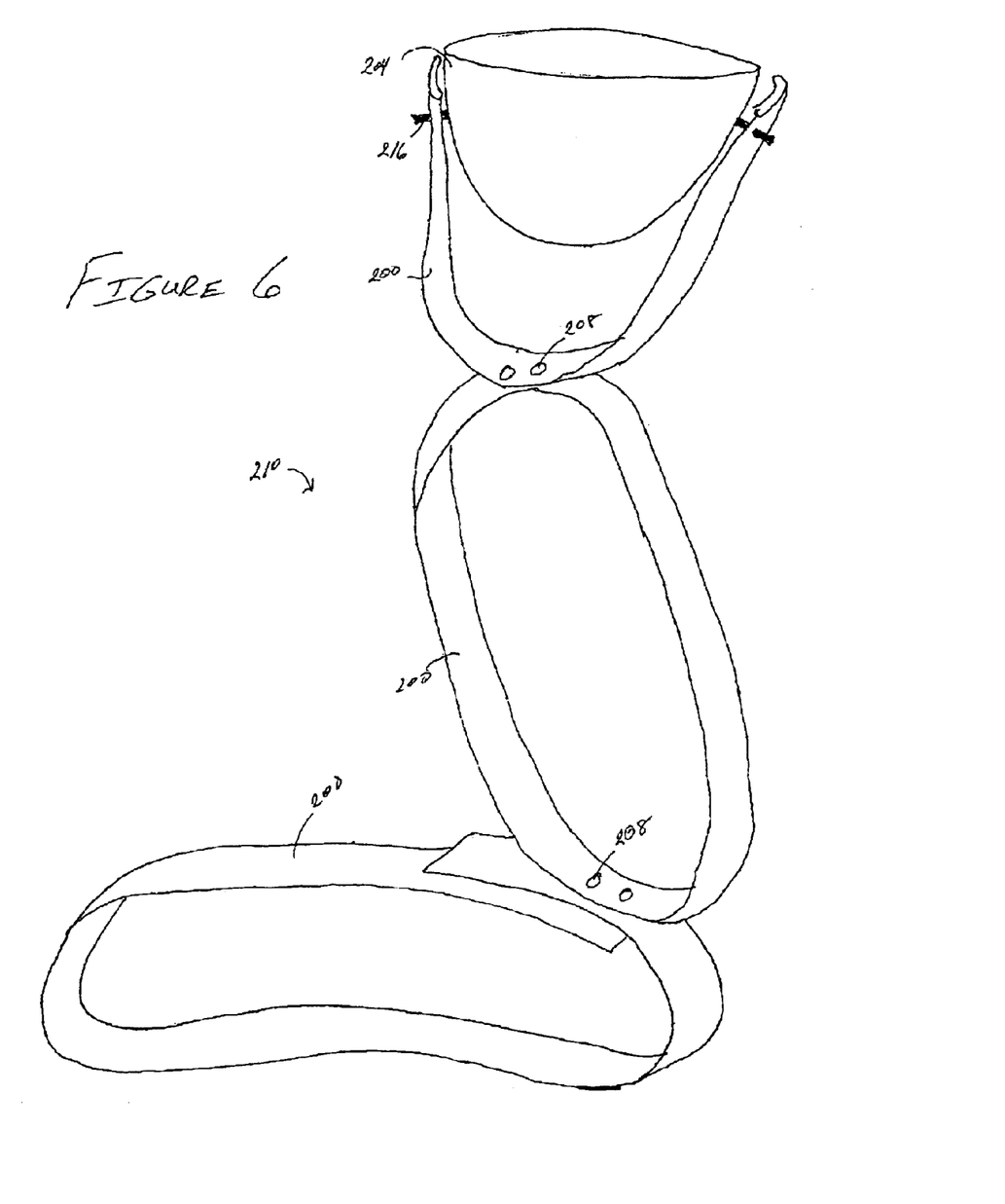
FIG. 6 shows a perspective view of an artificial leg embodiment fabricated from three superelastic supports formed to provide dynamic response at the ankle and knee regions.

FIG. 6 shows a perspective view of an alternative artificial leg embodiment 210 that incorporates three superelastic supports 200, the first defining the foot, the second defining the shin, and the third defining the calf. The attachment region between the first and the second superelastic supports defines a flex region mimicking the natural deflection of an ankle. The attachment region between the second and the third superelastic supports defines a flex region mimicking the natural deflection of a knee. The superelastic support 200 defining the calf region is attached to a leg securing mechanism 204 using attachment means 216 as previously described. The ends of each superelastic support are bonded together to enclose each superelastic support into a complete loop. Incorporating multiple superelastic supports to mimic natural flex points of anatomic joints improves the performance of the artificial leg by providing more realistic movement of the artificial leg and giving the wearer feedback that improves balance. It should be noted that more than three superelastic supports 200 may be used and the additional superelastic supports 200 may be formed so they intersect the original superelastic supports 200 at different locations. Incorporating multiple superelastic supports may provide enhanced lateral support, an improved stiffness profile at the flex points of the artificial leg, and/or heightened spring characteristics of the artificial leg.

Figures 7A, 7B:
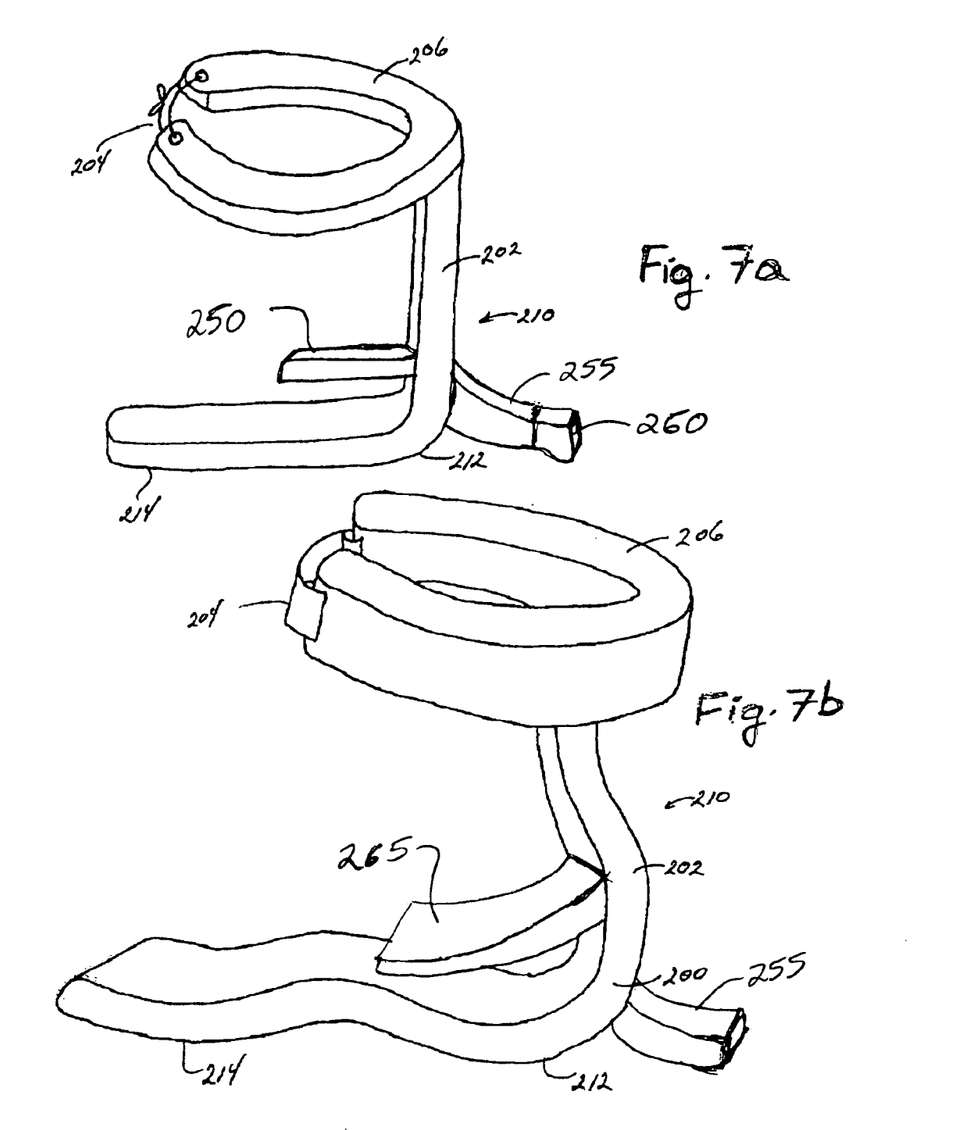
FIGS. 7a and 7b illustrate an artificial foot having forward and reverse stops.

FIGS. 7a and 7b illustrate the use of superelastic stabilizers with the artificial limbs. For example, FIG. 7a illustrates a forward stop 250 and a reverse stop 255. The forward stop 250 contacts the toe region 214 or other part of the "foot" when the wearer of the artificial limb 210 leans too far forward. The reverse stop 255 extends from the "heel" of the artificial limb 210 and stabilizes the wearer of the artificial limb, for example, from leaning too far backwards. The reverse stop 255 may optionally include a bumper stop 260, such as a removable rubber stop that can be replaced as it wears out after repeatedly contacting rough surfaces. FIG. 7b illustrates a forward stop 265 that curves forward in the direction of the toe region 214. Varying the angle of the forward stop 265 relative to the spring link 202 controls the amount by which the wearer can lean forward.

Figure 8:
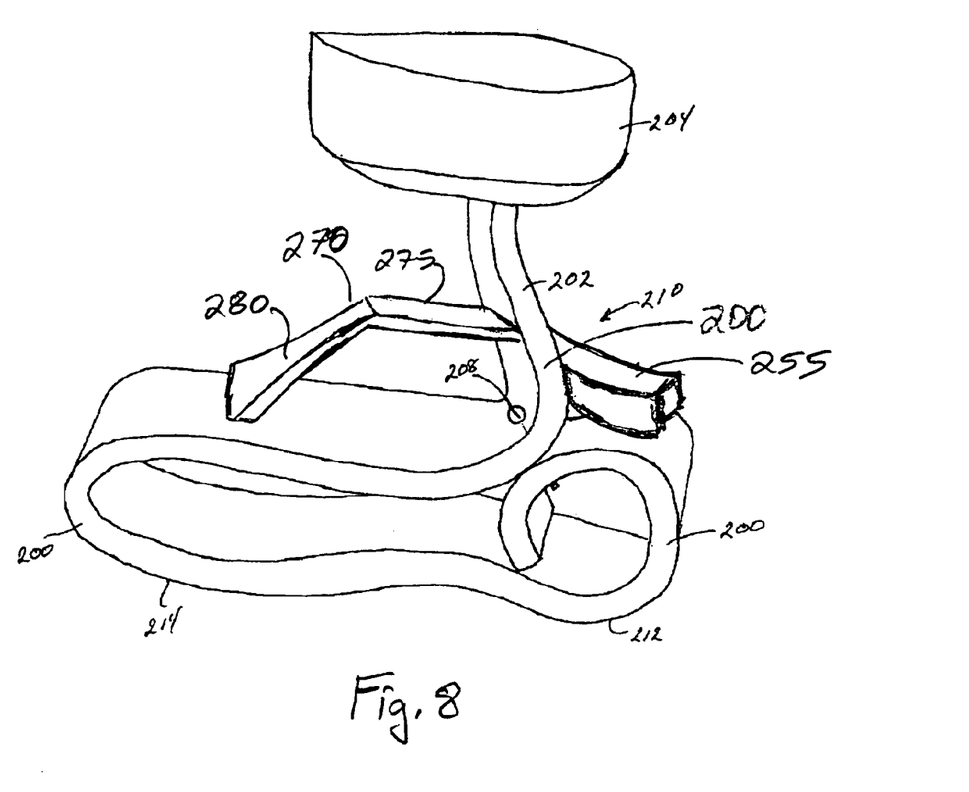
FIG. 8 illustrates an artificial foot having an angled forward stop.

Referring to FIG. 8, a forward stop 270 includes a first section 275 and a second section 280. The first section 275 extends generally perpendicularly from the spring link 202 and the second section 280 extends angularly from the first section in the general direction of the toe region 214. This configuration provides early tactile feedback to the wearer of the device that they are leaning forward and can provide an indication useful in maintaining balance and stability.

Figure 9:
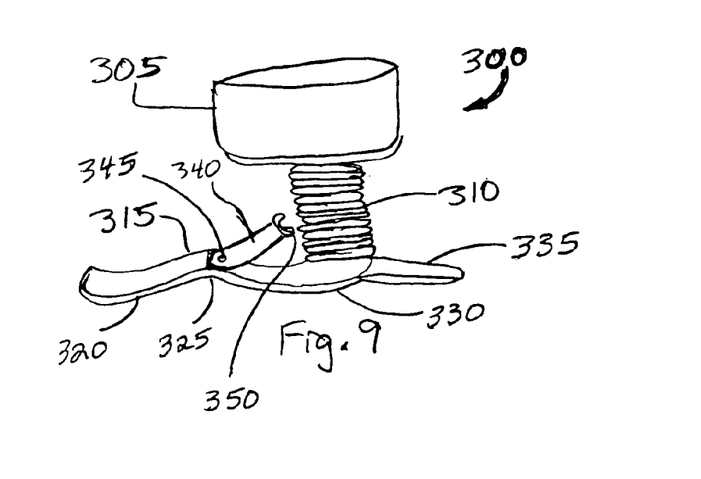
FIG. 9 illustrates an artificial foot having a coil or spring in the ankle member.

Referring to FIG. 9, an artificial limb 300 configured as an artificial foot includes a mounting end 305 configured to be mounted to a body part and one or more superelastic members (e.g., spring link). The superelastic members can be one or more of an ankle member 310 and a foot member 315. The ankle member 310 extends from a first end from the mounting end 305 and connects at an opposite end to the foot member 315. The foot member 315 includes a toe region 320, an arch region 325, and a heel region 330. A reverse stop 335 extends from the heel region 330 and a forward stop 340 extends from the arch region 325. The forward stop 340 is connected to the arch region 325 by a connection 345, such as any of the connections described herein. The forward stop 340 also includes a curved member 350 that is configured to mate with the ankle member 310 when the wearer of the artificial limb 300 leans forward. The superelastic members may be configured in any of the manners described above. Moreover, like the ankle member 310, they can be configured as a spring or coil.

The superelastic support structures previously described for the artificial limb embodiments above may additionally be modified accordingly for artificial hands, arms below the elbow, arms extending above the elbow, and arms including the shoulder. Similarly, the superelastic support structures may be formed as braces that reinforce nonfunctional or injured appendages. By changing the shape of the superelastic supports so they reinforce the appendages as opposed to replacing them, as required for artificial limb embodiments, the superelastic braces help restore motion of the appendage and improve the forces exerted by the appendage during desired activities.

The artificial limbs or braces may incorporate coverings to provide padding to the device, improve the aesthetics, or other purpose. Any artificial limb section, or the entire device may be covered with one or more coverings. For example, the base of the artificial limb may incorporate a sole material bonded to the ground contacting section of the limb for abrasion resistance, increased cushioning, improved traction, or other reason (e.g. the bottom of the artificial limb may resemble the aesthetics and functionality a shoe). Any conventional shoe sole material may be bonded to the superelastic supports using ultrasonic welding, adhesive bonding, thermally welding, radio-frequency welding, laminating, or other process. For example, the artificial limb or brace sole may be fabricated from phylon, TPU (thermoplastic urethane), TPVR (thermopolyvinyl resin) TPR (thermoplastic rubber), EVA, polyurethane, napos, PEBAX™, carbonized rubber, other conventional sole materials, silicone, elastomer, other polymer, or a combination of these materials. The sole maintains the position of the superelastic supports and permits the desired deflection of the superelastic supports while preventing degradation of the supports. Regions other than the base of the artificial limb or brace may also incorporate at least one covering (not shown). The covering may be fabricated from neoprene, fabric mesh, LYCRA™, SPANDEX™, leather, rubber, PEBAX™, nylon, polyester, other cushioning material typically used in anatomic braces and demonstrating excellent elasticity, or a combination of these materials. The artificial limb or brace superelastic supports may be inserted between layers of the covering materials. The layers of the covering then may be bonded together using adhesives, ultrasonically welding, thermally welding, radio-frequency welding or other bonding process.

Superelastic supports are also applicable to multiple artificial limbs collaborating to restore motion of replaced appendages to ensure the wearer can perform daily activities such as walking, running, standing, etc. The primary benefit of superelastic supports in artificial limbs over rigid components is that the superelastic supports induce a spring force upon external deflection of the superelastic supports. As such, a separate mechanism, such as a pull cord, may be used to induce the external deflection of the spring links of the artificial limbs and cause the desired dynamic response. For example, if a paraplegic desires to walk, the wearer applies tension to the pull cord causing deflection of the spring link for one of the artificial limbs or braces, then applies tension to the pull cord of the other artificial limb or brace while releasing tension to the first. These sequential actuations cause the wearer of the artificial limb to walk. Similarly, the wearer may bend down to pick up an object, and rely on the elastic recoil of the spring links to straighten the artificial limbs and cause the wearer to stand. Other artificial limb and brace designs are unable to apply a spring force in response to a deflection.

The superelastic supports incorporated in the artificial limbs (or other anatomic braces) may be fabricated from a flat sheet cut into the desired pattern of tightening links (e.g., tightening link 206) and spring links (e.g., spring link 202). Alternatively, the superelastic supports may be fabricated with a combination of flat sheet material cut into the desired; pattern and wires attached to regions of the flat sheet material.

The properties of the superelastic supports or structures described above may be varied to address applications in which the stiffness or elasticity needs to be varied accordingly. The composition of the superelastic material may be chosen to select the temperature range in which the support members or structures exhibit stress-induced martensite. As such, the amount of austenite, and stress-induced martensite characteristics throughout a specific temperature range may be chosen to specify the degree of deflection and amount of force exerted by the superelastic support member once deflected. For example, the superelastic properties of the material may be chosen so as exercise (or other activity) increases, the associated temperature increase induces a change in the superelastic properties of the superelastic support member or structure to provide, for example, increased rigidity and/or elasticity of the material.

The various artificial limbs, and braces described above may incorporate additional components such as magnets, padding, cold packs or drug-eluting coverings to further enhance the performance of the brace and scaffolds for their intended purposes.

While several particular forms of the invention have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Moreover, although many of the components of the artificial limbs have been described as being made from superelastic materials, such as Nitinol, the artificial limbs can have components made from carbon and/or Kevlar fiber composites. For example, the spring link can be made from Nitinol and the foot portion can be made in part or in whole from a carbon fiber composite. Accordingly, it is not intended that the invention be limited, except as by the appended claims.

We claim:

1. An artificial limb comprising:
   a mounting end configured to be externally mounted to a patient's body; and
   one or more superelastic members, whereby in use of the artificial limb, pressing the artificial limb against a surface applies a force of flexing to the superelastic members and causes the superelastic member to flex from a first position to a second position and upon removal of the force of flexing the superelastic member returns to the first position.

2. The artificial limb of claim 1, wherein at least one of the superelastic members are connected to the mounting end.

3. The artificial limb of claim 1, wherein a first superelastic member includes a curved section.

4. The artificial limb of claim 1, wherein the one or more superelastic members comprises Nitinol.

5. The artificial limb of claim 1, wherein the one or more superelastic members comprise a pair of generally parallel superelastic members.

6. An artificial limb comprising:
   a mounting end configured to be mounted to a patient's body;
   a first superelastic member; and
   a second superelastic member extending from the first superelastic member, whereby in use of the artificial limb, pressing the artificial limb against a surface applies a force of flexing to the superelastic members and causes the superelastic member to flex from a first position to a second position and upon removal of the force of flexing the superelastic member returns to the first position.

7. The artificial limb of claim 6, wherein the first superelastic member has a first orientation, the second superelastic member has a second orientation, and the first orientation is generally perpendicular to the second orientation.

8. The artificial limb of claim 6, wherein the second superelastic member includes a curved section.

9. The artificial limb of claim 6, wherein the second superelastic member comprises Nitinol.

10. The artificial limb of claim 6, wherein the second superelastic member comprises a pair of generally parallel superelastic members.

11. The artificial limb of claim 6, further comprising a third superelastic member extending in a generally perpendicular direction from the first superelastic member, whereby a force of flexing the first superelastic member in the direction of the second superelastic member is counteracted by the third superelastic member contacting the second superelastic member.

12. A method of using an artificial limb comprising:
    mounting an artificial limb to a patient's body, the artificial limb comprising a mounting end configured to be mounted to a body part and one or more superelastic members;
    applying a force to the artificial limb to deflect the artificial limb from a first position in a first direction; and
    removing the force, whereby the artificial limb moves to the first position, wherein applying a force to the artificial limb comprises pressing the artificial limb against a surface.

13. The method of claim 12, wherein mounting an artificial limb to a body part comprises placing a tightening link around the body part.

14. The method of claim 12, wherein mounting an artificial limb to a body part comprises inserting the body part into a concave housing.

15. The method of claim 12, wherein applying a force to the artificial limb comprises bending the one or more superelastic members.

16. The method of claim 12, wherein the one or more superelastic materials comprise Nitinol.

* * * * *